United States Patent [19]
Tikhtman et al.

[11] Patent Number: 5,646,358
[45] Date of Patent: Jul. 8, 1997

[54] HIGH ACCURACY WEATHERING TEST MACHINE

[75] Inventors: Jacob Tikhtman, Northbrook; Bhakti S. Patel, Bensenville, both of Ill.

[73] Assignee: Atlas Electric Devices Co., Chicago, Ill.

[21] Appl. No.: 594,154

[22] Filed: Jan. 31, 1996

Related U.S. Application Data

[62] Division of Ser. No. 393,060, Feb. 23, 1995, Pat. No. 5,503,032.

[51] Int. Cl.$^6$ ................................................. G01N 17/00
[52] U.S. Cl. .......................... 73/865.6; 73/159; 165/259
[58] Field of Search .................... 73/159, 865.6; 219/663, 665, 667; 165/26

[56] References Cited

U.S. PATENT DOCUMENTS

| | | | |
|---|---|---|---|
| 4,627,287 | 12/1986 | Suga . | |
| 4,817,447 | 4/1989 | Kashima et al. | 73/865.6 |
| 4,843,893 | 7/1989 | Huber et al. . | |
| 4,957,011 | 9/1990 | Huber et al. | 73/865.6 |
| 5,209,398 | 5/1993 | Drees . | |
| 5,226,318 | 7/1993 | Huber et al. . | |
| 5,253,564 | 10/1993 | Rosenbrock et al. . | |
| 5,349,167 | 9/1994 | Simcock | 219/667 |

*Primary Examiner*—Robert Raevis
*Attorney, Agent, or Firm*—Gerstman, Ellis & McMillin, Ltd.

[57] ABSTRACT

A weathering testing machine or the like is provided with improved stabilization of conditions such as temperature and humidity, coupled with more accurate readout from sensors on a moving member in the machine, and other sensors and microprocessors.

4 Claims, 3 Drawing Sheets

HIGH ACCURACY WEATHERING TEST MACHINE

This is a division of application Ser. No. 08/393,060, filed Feb. 23, 1995, now U.S. Pat. No. 5,503,032.

BACKGROUND OF THE INVENTION

Systems for testing materials, for example the weathering and lightfastness of products such as fabric samples, painted panels, and plastics, are presently available, being sold for example by the Atlas Electric Devices Company of Chicago, Ill. Also, such devices are disclosed in Suga U.S. Pat. No. 4,627,287, and Huber et al. U.S. Pat. Nos. 4,843,893 and 5,226,318, for example. Weathering testing devices test the weathering and lightfastness properties of materials and products under closely controlled conditions.

In the natural environment, heat, light, and moisture combine synergistically to cause optical, mechanical, and chemical changes in products which are exposed to outdoor weathering conditions. Typically, the testing apparatus of this invention and the prior art can be used to obtain such weathering data on an accelerated time basis, to permit product manufacturers to gain information as to how their products will stand up to weathering over the months or years.

Typically, a weathering testing apparatus may use air which circulates through the system to control the temperature of samples being tested, so that they are not underheated or overheated by a heater or radiation source which may be present, typically a high intensity plasma lamp such as a xenon lamp. It is desirable for the samples being tested to be exposed to precisely predetermined conditions, to permit more accurate comparison between various testing runs and the like, and so that the weathering conditions provided by a weathering tester can be accurately predetermined and thus recreated when desired for comparison of various samples over the years, and the like.

By this invention, improvements are provided which increase the accuracy of the testing machine of this invention, in that the machine can be used to provide accurately predetermined conditions which are substantially predictable and invariant throughout a run and from run to run, and also in that temperature and other measurements may be more accurately made, even from sensors which are carried on a moving test rack carried in the enclosure of the testing machine.

By this invention more accurate results, with better reproducability, can be obtained concerning the lifetimes of materials and other testing issues.

DESCRIPTION OF THE INVENTION

By this invention, in one aspect thereof, a method is provided of controlling temperature in a testing chamber having a heater and a variably openable and closeable air inlet vent. The vent is controllable by a first controller and a first temperature sensor in the chamber. The controller serves to open and close the vent responsive to the temperature sensed by the first sensor. By the method of this invention, one selects, preferably automatically, a first vent position that is more open than a mean or average vent position that provides a desired temperature in the chamber under a first set of operating conditions, as determined by the first controller and first temperature sensor. One then fixes the vent in that first position. Thereafter, one controls the temperature entirely by the heater.

The advantage of this invention can be seen from the following background: In Huber et al. U.S. Pat. No. 4,843,893, a weathering testing system is shown which has a temperature sensor that automatically controls the position of a damper or vent in an air circulation flow path which circulates air through the chamber of the weathering testing system. Thus, as the temperature rises, it is sensed by the sensor. The sensor will signal for the damper to be opened to a degree that causes more cooling air to enter the system, thus reducing the temperature and providing a feedback loop control.

In other prior art systems, both the damper and the heater are controlled by a single loop of a controller, so that the damper opens and the heater reduces its production of heat as the temperature rises, while the damper closes and the heater increases its heat production as the temperature drops.

Testing systems having chambers with these types of control systems tend to have temperatures that oscillate, as the damper and the heater work in conjunction with the sensor in a continuing attempt to stabilize the temperature of the chamber at a desired level. Of course, the turbulence of new air brought in from the damper causes nonstandard temperature regions to briefly form. Likewise, humidity can be significantly affected by the operation of the damper, so that undesired oscillations in both humidity and temperature take place, typically about a mean value. This causes corresponding oscillations of the degree of damper opening and heater activity about mean values.

By the method of this application, the approximate mean (or average) position of the oscillating damper is determined for obtaining a desired temperature at the specific operating conditions which are being used in the weathering testing machine. Such operating conditions include the desired temperature, the desired humidity, the blower speed used, the intensity of the radiation source used, and the like.

One then fixes the position of the damper in a first vent position that is slightly more open than the mean or average of the range of oscillating damper positions in the vent which are conventionally provided by the first controller and first temperature sensor in the chamber. This mean or average position and the slightly more open position can be automatically computed.

This immediately stabilizes the conditions in the operating testing chamber, but typically going toward an equilibrium temperature that is slightly cooler than desired.

The first vent position is typically only slightly more open than the mean or average vent position, with the first vent position desirably providing no more than about 10 percent more cooling air to the chamber than is required to maintain the desired temperature under a first set of operating conditions of the testing chamber. Thus, to maintain the desired temperature, the heater will tend to produce a little more heat than in the prior art mode of operation under similar conditions, but significant improvements in the stability of the conditions will be achieved, for testing results of improved accuracy.

The heater can be controlled by the first controller, responsive to the same signals from the first temperature sensor as is the damper, if desired, for a simplification of parts and circuitry.

Also, it is preferred for a blower motor to be present to blow air through the chamber, and for second controller and a second temperature sensor to be present, to control the blower motor speed dependent upon signals from the second temperature sensor. Typically, the first temperature sensor is positioned to sense primarily air temperature, being remote from a central, radiant energy source in the chamber. The second temperature sensor may be a black panel sensor, positioned to primarily sense temperature directly imparted by the radiant energy source in the chamber. Thus, as previously described in U.S. Pat. No. 4,843,893, simultaneous and somewhat separate temperature control of dark testing samples and light testing samples can be achieved, but by this invention under conditions which are very stable and which can be accurately reproduced.

In the event that the first temperature sensor senses a temperature that moves out of specified limits, indicating a loss of temperature control, the software of the system within the first controller can cause the damper to be released, to find a new oscillating set of positions of variable damper opening, and accordingly a new, mean damper position, provided by the first controller and temperature sensor in conventional manner. Then, after determining a new, mean position for the damper, the control can automatically select a slightly more open position as before, which in this circumstance is likely to be different from the earlier slightly more open position, and the damper can be set in stationary manner in the new position. Once again, conditions will be substantially stabilized, with the temperature control being governed exclusively by variations of temperature output in the heater.

Thus, a continuing, dynamic control system may be provided in which the position of the damper vent is locked in a stationary position as described above, except when the sensed temperature moves out of a specified range.

Then the system unlocks, and goes back to its original mode of temperature control as described above, following which the damper vent may be relocked in a new position for high stability temperature control whenever the damper vent is locked in a particular position.

Further in accordance with this invention, the testing chamber may be equipped with a source of humidity, typically a water spray nozzle as is conventional. By this invention, an improved method of providing and controlling the humidity levels to the testing chamber is provided, in which the testing chamber has a blower for circulating air in the chamber. By this invention, one provides a water spray nozzle, as stated, extending into the circulating air of the chamber. One then defines a unit of time, with the process of this invention being repeated in sequential units of time as defined. Typically, such a unit of time is no more than about thirty seconds and preferably no more than about 10 seconds.

One periodically determines the humidity of the air in the chamber. One then compares the difference of the humidity of the air in the chamber with a desired or set humidity objective. The water spray is applied to the chamber through the nozzle for a portion of the unit of time down to zero percent, which portion is dependent on the compared humidity difference as described above, which may be electronically compared and calculated.

The water spray is not provided or applied to the chamber for the remainder of the unit of time. For example, 5 to 30 percent of the unit of time may comprise the "on" mode of the spray nozzle, in which spray is being inserted into the chamber, and the balance of the unit of time may comprise the "off" mode, in which water spray is not being added to the circulating air of the chamber.

The process is repeated in subsequent units of time, preferably in each adjacent, sequential unit of time, to provide a consistent, pulsed application of water spray to the circulating air throughout the operation of the testing chamber. However, if desired, longer gaps in the spray application over time may be provided if desired.

By this invention, a significant improvement in the uniformity of the humidity imparted to the chamber may be achieved. The specific humidity imparted may depend if desired on a single variable: the percentage of unit of time in which the spray is activated. Such high uniformity provides excellent reproducability of humidity conditions from testing run to testing run, plus the precise humidity that is desired, without significant variation due to unstable and non-standard conditions.

Particularly, the uniformity of humidity provided by this invention comprises a substantial improvement over methods in which a humidity sensor activates a water spray or atomizing nozzle for continuous operation when the sensor senses an undesirably low humidity, and then shuts off the water spray when the sensor detects proper humidity. In such procedures there is often a humidity overshoot, in which the humidity rises beyond the desired level in non-uniform manner, contrary to the humidification method disclosed herein.

In similar manner, by this invention a heater in a testing chamber having a blower for circulating air in the chamber may provide heat to the system in accordance with the following method: one defines a unit of time similar in concept and use to the unit of time previously discussed with respect to the humidification process. One periodically determines the temperature of the air in the chamber, then comparing the difference of the temperature of the air in the chamber with a desired or set temperature. One activates the heater (by turning on the electric power if the heater is electric) for a portion of the unit of time, which portion is dependent upon the compared temperature difference described above. The particular portion may by computed electronically in a manner believed to be readily understandable by those skilled in the art. Then, one does not activate the heater (e.g. the power is off) for the remainder of the unit of time.

Here also, this process is repeated in subsequent units of time to provide a pulsed application of the heater, typically over a continuing series of adjacent units of time, which units are typically no more than about 30 seconds in length and preferably no more than about 10 seconds. Thus, for example, a heater may be activated for one or two seconds out of every 10 second period of time that elapses throughout the testing process that is taking place in the testing chamber. Such an application of heat provides high uniformity of temperature conditions throughout the testing chamber.

As previously described, the heater is responsive in its operation to the first sensor and first controller. When the air temperature is sensed to be falling below the desired level, the controller can cause the heat energy to be provided to the heater for a larger portion of each unit of time. If the temperature rises above the desired limits, the heat energy can be provided to the heater for a smaller portion of each unit of time. The same principle applied in the previously-described humidity control process.

Thus, further improvements in the uniformity of test chamber conditions can be achieved.

As a further embodiment of this invention, a weathering testing system is provided which comprises a chamber and a rack for carrying samples to be tested. The rack, in turn, defines a central space. A lamp is located centrally in the rack for irradiating samples carried on the rack. A blower is provided for directing a stream of air through the rack.

The chamber has top and bottom walls. The rack is carried by a support member, typically a rotatable shaft, which extends through the top chamber wall. The lamp is carried by a second support member which extends through the bottom chamber wall, with the lamp being spaced from the top chamber wall and thus isolated therefrom. Typically, the rack is spaced from the bottom chamber wall.

The typical electronic sensors (such as temperature, humidity, light sensors) which are carried by the rack may communicate along or through the first support member, which extends through the top chamber wall, being thus isolated from the heavy electric currents and cooling water which are typically provided to the lamp. The lamp electric circuitry and any cooling water circuitry present extends downwardly along or through the second support member, passing through the bottom chamber wall.

This provides the sensitive circuitry and sensors which may be carried by the rack, with isolation from the heavy electric currents of the lamp, reducing the electrical noise encountered in the sensitive sensor circuits and the like of the rack, and also isolating the electronic components associated with the rack from any water that escapes from water lines.

Thus, the data gathering capability of the testing machine of this invention can be improved over prior art systems by the reduction of electrical noise as well as a reduction of damage, caused by inadvertent water migration, to the electronics of the system.

Further in accordance with this invention, an improved method of determining data on a moving test member is provided. Specifically, the rotating rack described above may comprise the moving test member, with the data being picked up by the first and second sensors, or other devices, as may be desired.

In accordance with the method, one operates an electric circuit which is at least partially carried on the test member. The circuit comprises a sensor device having a resistance that varies as a function of the data to be determined, for example a variable resistance temperature sensor, to provide a first signal in the circuit which carries the data. One then converts the first signal into a variable current signal in which the current of the signal is a function of the first signal, so that the variable current signal carries the data to be determined in the variability of the current.

One then passes the variable current signal through a typically conventional collector or collectors from the moving test member to a stationary control system, which is spaced from the test member. The current variations of the variable current signal are then converted into the data in a useable form, for example a numerical data value of the temperature sensed, in degrees Celsius.

By this technique, it becomes possible to provide the data to the user in an absolute, quantitative, error-free form rather than merely a relative data readout.

Prior art systems for determining data from a moving rack in a testing chamber provide a Voltage dependent signal as a function of the variable resistance of the sensor device described above. This voltage dependent signal is passed through a collector to the stationary control system, with the data being a function of the voltage sensed.

However, the voltage can be varied by the resistance of the collector, which can change from day-to-day, so that the data provided may have errors, requiring frequent calibration of the system against an objective standard. One reason for this is that collectors, which are known devices for passing electric current from a moving system to a stationary system using brushes against a moving surface or an electrode in contact with mercury, will vary in their resistance with time. This results in significant voltage variations of the signal as a function of the collector itself, which renders the data inaccurate, and only useable on a comparative basis.

By this invention, for the first time in the field of testing chambers, error-free temperature and other data may be acquired from devices carried on a rotating rack or the like. This is accomplished as described above by providing a signal which leaves the moving rack through a collector and is directed to the stationary control system, which signal has a controlled current (in amperes) which depends entirely upon the resistance value which is found in the variable resistance device. Through the conventional electronics used, the voltage of the signal may vary or be constant as necessary to achieve this predetermined current for the signal. Thus, an objective value that is a pure function of the variable resistance sensor is provided to the control system, where it may be conventionally converted into a numerical readout of temperature or the like, being an absolute value without need for correction of errors introduced by the electronics.

DESCRIPTION OF SPECIFIC EMBODIMENTS

Figure 1:
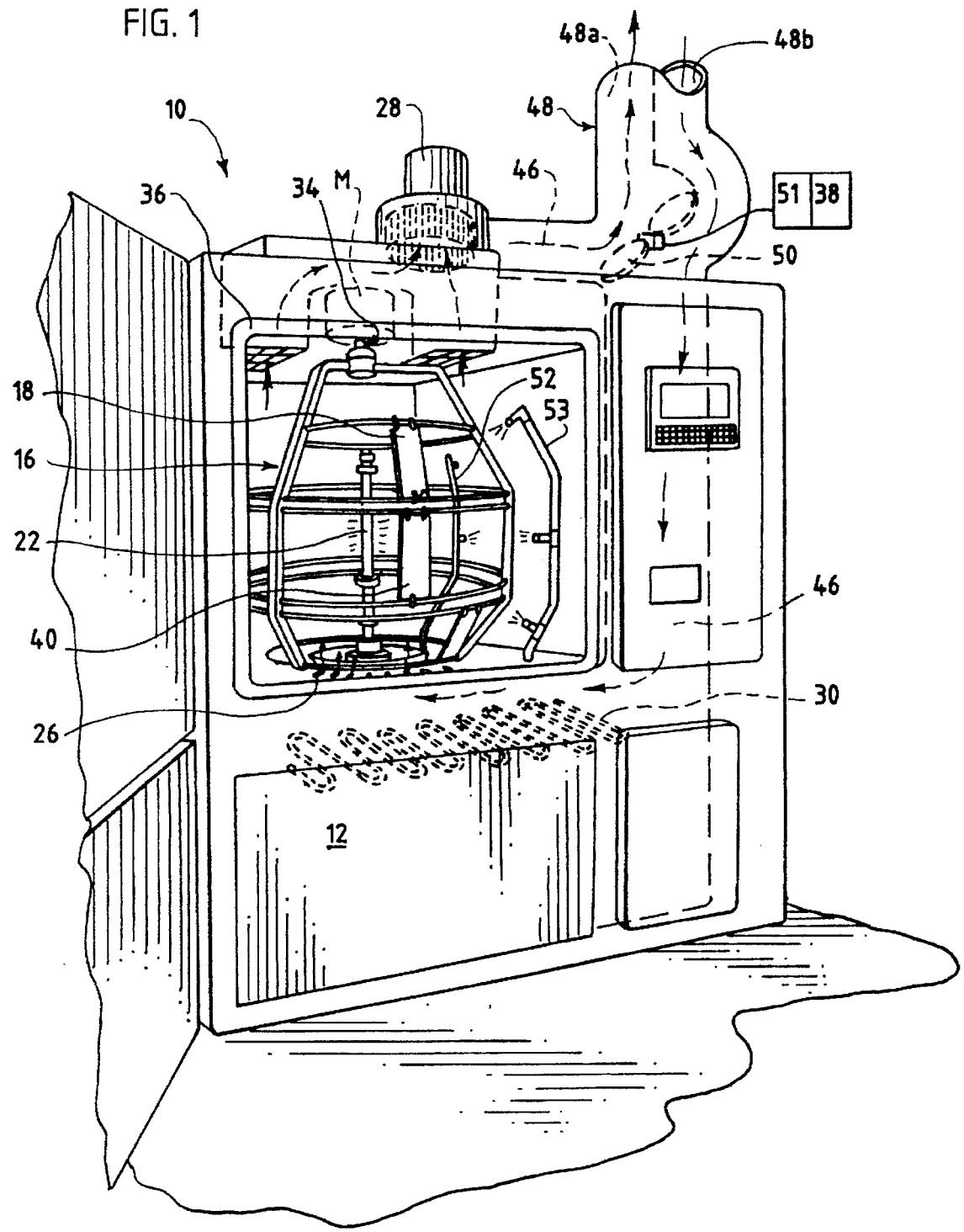
FIG. 1 is a perspective view of a weathering testing system in accordance with this invention.

Referring to the drawings, a weathering testing device 10 is shown, which comprises a housing 12 defining an upper chamber 14 in which a rack 16 resides, comprising a roughly spherical array of stainless steel struts, to which test samples 18 may be attached in a manner substantially equidistant from a central light source 22, which may be a xenon lamp. This arrangement is similar to that disclosed in U.S. Pat. No. 4,843,893.

At the bottom of upper chamber 14, a circular arrangement of apertures 26 are provided, plus a conical baffle 24 to assist in directing air passing through apertures 26 along the test samples 18 carried on the rack.

Figure 3:
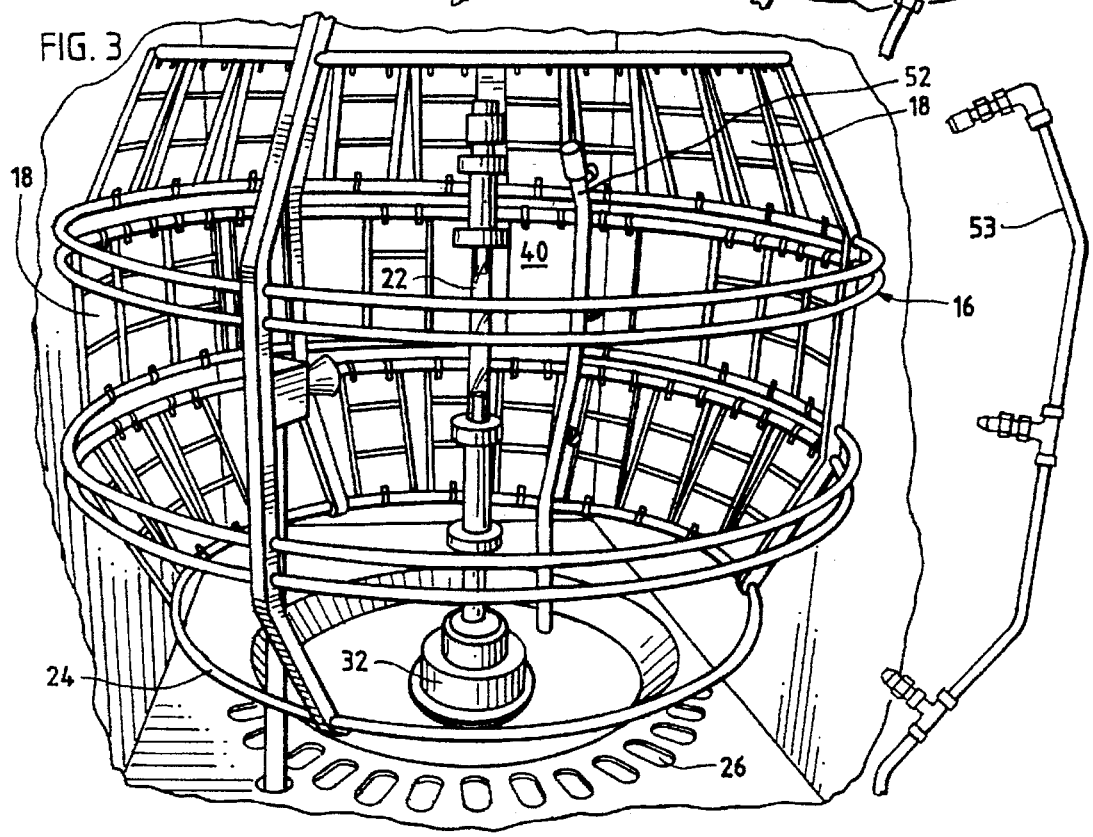
FIG. 3 is a perspective view showing a lower portion of the upper compartment of FIG. 1.

A conventional resistance type heater element 30 is positioned under the apertures 26 and the partition that carries them. Also, a fitting 32 (FIG. 3) for xenon lamp 22 is provided, being adjustable and designed in accordance with U.S. Pat. No. 5,226,318. Fitting 32 includes both electrical and water flow conduits for servicing the xenon lamp 22, while xenon lamp 22 is spaced from the top of upper chamber 14. Lamp fitting 32 is also named the "second support member" above.

Figure 2:
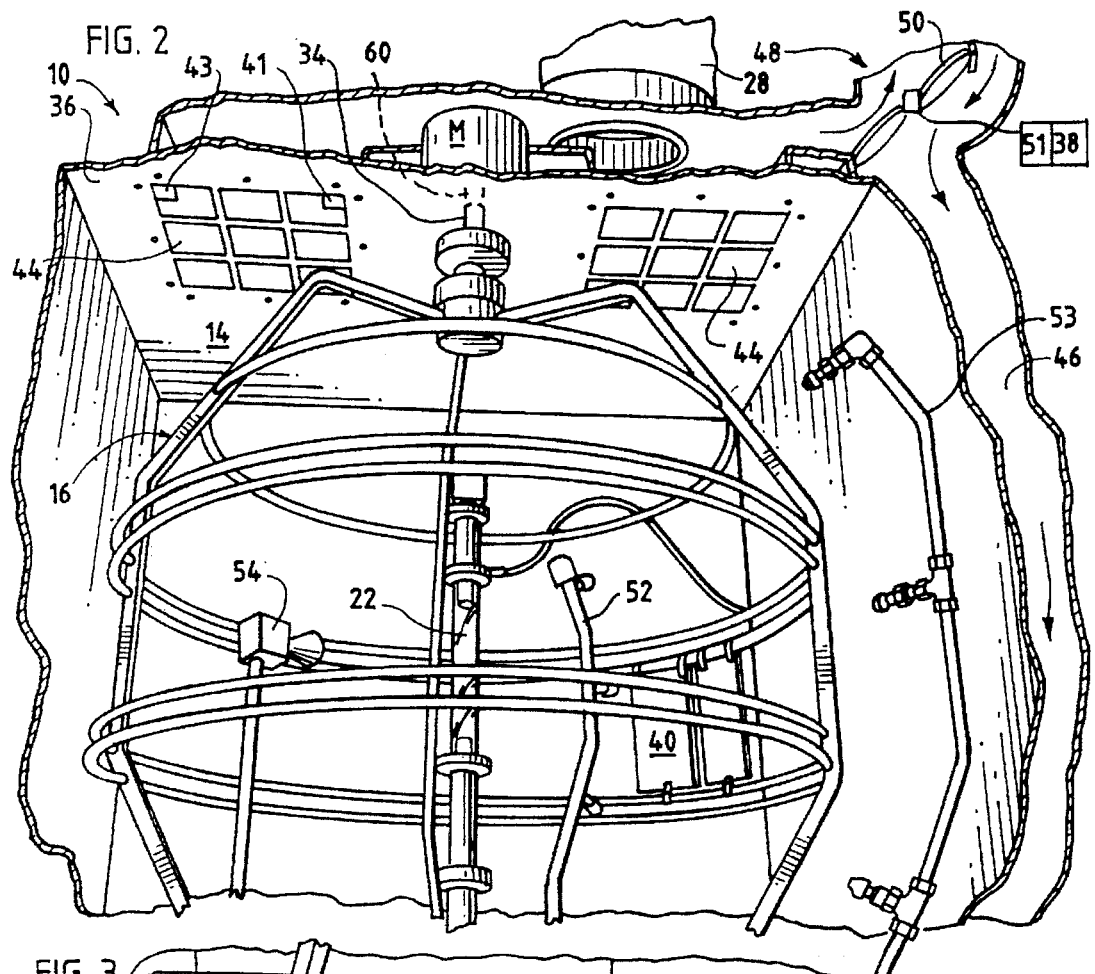
FIG. 2 is a perspective view showing the upper portion of the upper compartment of the weathering tester of FIG. 1.

Rack 16 is carried by a first support member or shaft 34 which extends through the top wall 36 of the upper chamber 14. Thus, the connections of various electronic devices carried on rack 16 may pass with shaft 34 through top wall 36 to a microprocessor 38 (FIG. 2) that is carried on the weathering testing system above top wall 36, in a manner that is safely spaced from both the flowing water and the high electric currents and voltages used with respect to xenon lamp 22.

Also, a motor M is positioned above top wall 36 which rotates shaft 34 and lack 16, when that is desired during the weathering testing process.

Test rack 16 may carry a black panel temperature sensor 40, which is a sensor particularly adapted to sense the temperature directly imparted by the radiation from the xenon lamp. This sensor models the temperature conditions encountered by darker samples carried on the rack. Dry bulb sensor 41 is provided in a position more remote from lamp 22, to monitor air temperature. Also, a direct percentage RH humidity sensor 43 is provided. Each of these provide signal data to microprocessor 38.

Top wall 36 also defines wall apertures 44 which represent the inlet of a circulatory plenum 46 that circulates air, driven by blower 28, from the top to the bottom of chamber 14 and through apertures 26, as propelled by blower 28.

Within plenum 46 is a variably openable cooling air supply vent 48 having a movable damper 50, and comprising air inlet. 48a and air outlet 48b. The position of the damper 50 can be controlled by a control member 51 which is, in turn, controlled by the microprocessor 38 in a conventional manner.

Rack water spray or atomizer unit 52 is also provided in upper chamber 14, along with a light sensor 54, which directly monitors the radiation emission of the xenon lamp. Also, a specimen water spray or atomizer unit 53 is provided for added specific spraying of the specimens when that is desired.

In accordance with one aspect of this invention, lamp 22 is mounted in a bottom fitting 32 which may be similar in structure and function to the corresponding fitting disclosed in U.S. Pat. No. 5,226,318, except that fitting 32 is mounted on the bottom wall of chamber 14 rather than the top wall so that lamp 22 extends upwardly therefrom and is spaced from the top wall 14.

Also, as shown, rack 16 is suspended from the top wall 14, being carried by shaft 34, and being spaced from the bottom wall of the chamber.

Accordingly, as previously described, the electronics of the system, exemplified by microprocessor 38, can be well spaced from the high voltage and amperage inlet and water inlet which feeds from the bottom of the chamber upwardly in otherwise conventional manner, to space the high electric currents and water from the sensitive electronics of the system.

Further in accordance with this invention, one controls the temperature in testing chamber 14, making use of heater 30 and a variably openable and closeable cooling air inlet vent 48 which has a damper 50 which is variably openable and closeable by a first controller 51. The first controller comprises a controller motor which is operated by signals from microprocessor 38. Microprocessor 38, in turn, processes signals from typically temperature sensor 43 to cause the damper 50 to assume a position intended to stabilize the circulating air temperature at a desired value.

However, as previously described, what typically happens in actuality is that the temperature readings oscillate, causing the damper to oscillate about a mean vent position. The effect of this is an undesirable instability of air temperature.

In accordance with this invention, microprocessor 38 determines a mean or average vent position in an empirical manner over a specified period of time, perhaps two to three minutes, this being accomplished by any manner which is obvious or desirable to those skilled in the art of computer programming. Then, a first damper position is selected by the microprocessor, which preferably places the vent about 10 percent more open than the computed mean position, and the damper is temporarily fixed in that new position without further motion. Thus, as the air circulates through plenum 46, impelled by motor 28, the temperature oscillations caused by the feedback between the signals sent by temperature sensor 41 to processor 38, and the oscillations of damper 50, are stabilized,.although at a damper position which can be expected to cause more fresh air to enter the system than that amount required to maintain the desired temperature under the particular conditions of operation such as blower speed, lamp energy production, and the like.

Thereafter, heater 30, which also may be controlled by microprocessor 38, serves as the only temperature control in an otherwise-stable system, so that precise, uniform, reproducible air temperature control can be provided in a system of stable variables except for the production of heat, at a stable damper setting that closely approximates the damper setting appropriate to the desired temperature. This can be accomplished through an automated system which spontaneously determines the desired damper position and which spontaneously controls the heater 30 to provide a stable, predetermined temperature.

If the temperature is sensed by unit 41 to go out of a predetermined range, the software of microprocessor 38 once again releases the fixed position of damper 50, to go back into the feedback mode where the damper is responsive to moment-by-moment temperature signals from sensor 41. An oscillation of the damper 50 is once again likely to occur for a period of time until a new mean position for the damper is determined. At this time the process of this invention takes place again by fixing of the damper 50 at a predetermined position wider open than the mean position of the oscillating damper, to achieve the desired results discussed above.

Black panel sensor 40 also communicates by a wire which passes through or beside shaft 34, for electrical contact with microprocessor 38. The speed of blower 28 can, if desired, be controlled in a manner responsive to the temperature signals received from black panel sensor 40.

As the temperature in tester 10 originally warms up a minimum temperature set point may be used, at which point damper 50 opens slightly and is set to stay at least slightly open (about 5 percent) while the temperature is above the set point, to facilitate the temperature control through the blower 28 and back panel sensor 40.

Further in accordance with this invention, heating coil 30 can also be controlled in an automated manner from temperature signals received by sensor 41. This is accomplished by defining time into discrete, adjacent units of typically 5 seconds each. Sensor 41 sends temperature signals to microprocessor 38 which compares the signals with a desired temperature, and determines the difference of the temperature of the air in the chamber with that desired temperature. If the difference is zero, or sensor 41 senses a temperature higher than the desired temperature, then the microprocessor 38 does not activate heater coil 30 during the unit of time. However, if the microprocessor 38 determines that the temperature sensed by sensor 41 is below the desired temperature, then, the microprocessor will cause heater coil 30 to be electrically actuated for a particular percentage of each 5 second unit of time. This percentage may be directly dependent on the size of the temperature difference determined by the microprocessor, so that if the temperature sensed is 10 degrees or more under the desired temperature, then the heater coil 30 is energized for 100 percent of each 5 second increment or unit of time. However, as the difference between the sensed and the desired temperature gets smaller, the fraction of each unit of time in which the heater coil is energized for production of heat goes down until, when the sensed temperature and the desired temperature are the same, the heater coil 30 is energized for a predetermined fraction of each unit of time that tends to maintain the desired temperature.

By this means, accurate and reproducible temperature control with low deviations from the desired temperature can be achieved, avoiding the temperature overshoot of conventional control schemes.

In similar manner, the humidity provided to the circulating air in the chamber through spray or atomizer units 52, 53 can be controlled. Humidity sensor 43 communicates with microprocessor 38. The microprocessor 38 defines sequential units of time, which typically may be 5 second increments as in the previous control method for temperature. The difference between the sensed humidity and a predetermined humidity is determined. If the difference is zero, one or both of the spray nozzles 52, 53 are "on" during only that portion of each 5 second repeating unit of time needed to maintain the desired conditions, for example 20 percent of the time. Similarly, if the sensed humidity is higher than the predetermined humidity set in the microprocessor, the respective sprays may be off for each entire unit of time.

However, if the sensed humidity drops below the predetermined humidity, then the microprocessor 38 will signal one or both of sprays 52, 53 to turn on for an increasing portion of each of the respective units of time, with that portion increasing to 100 percent of each unit of time as the difference between the predetermined humidity and the sensed humidity is larger. Thus, a continuing but intermittent spray is provided for substantial stabilization of the humidity at a predetermined level, with greatly reduced fluctuation in the humidity as provided by the prior art techniques for applying water spray to the circulating air. This can be accomplished in a fully automated manner.

Further in accordance with this invention, signals from sensors carried on the rotating rack 16, for example black panel sensor 40, must pass across an electrical collector 60 carried about shaft 34 to permit electric signals to pass from the moving sensor 40 to the stationary microprocessor 38 or other electronic monitor and control system carried on the frame of the apparatus.

The conventional technique of accomplishing this uses a black panel sensor that may comprise a resistance temperature device such as a known RTD PT-100 unit, in which the electrical resistance thereof varies in accordance with the temperature sensed. The moving resistance temperature device (RTD) is joined in an electrical circuit with a stationary electric monitor and control system. The circuit passes through a pair of collectors, which may be standard devices for passing an electric signal from a moving member to a stationary member. For example, a collector using brushes or liquid mercury is well-known. The electronic monitor and control system monitors the voltage in the electrical circuit, which of course is dependent on the variable resistance of the resistance temperature device, to determine the temperature sensed by the resistance temperature device.

However, a significant problem in this prior art system lies in the fact that the resistance of the collector can also vary with use thereof, as well as with other factors. Thus, this system only provides a relative temperature value so that the electronic system must be frequently calibrated.

By this invention, an electronic system and method are provided for determining data in a moving test member, in which the data provided to a stationary control system outside of the moving test member is quantitative, without the need for frequent calibration.

Figure 4:
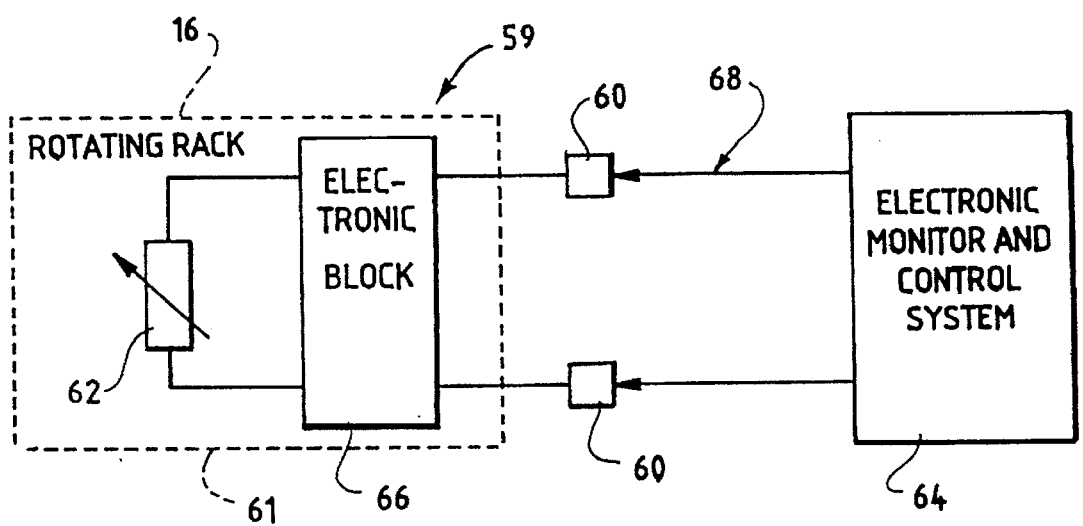
FIG. 4 is a diagrammatic view of a sensing system in accordance with this invention.

By this invention, referring to FIG. 4, one operates an electric circuit 59 having a portion 61 that is carried by the moving rack 16. This circuit portion comprises a resistance temperature device 62 which may be identical to the device used in the prior art, as part of the black panel sensor 40. Device 62 is electrically connected in a circuit to an electronic block 66, as a new element of the invention, which measures the resistance in the resistance temperature device 62 and produces a signal current in response thereto which is directly and exclusively responsive to the variable resistance of RTD 62, under the specific conditions of use. Such a device is known, and may be accomplished by many different electronic designs. Specifically, a Yakagawa signal transmitter (RTD to Current) JUXTA FR5A may be used as electronic block 66.

Electronic block 66 is connected in a circuit 68 with electronic monitor and control system 64 through collectors 60 which, as previously described, are conventional, and may be either brush collectors, liquid mercury collectors, or the like, to permit a moving electrical terminal to communicate with a stationary electrical terminal.

The signal which passes through circuit 68 between electronic block 66 and control system 64 has a predetermined amperage or Current, as determined by electronic block 66 in response to the resistance of device 62, while the Voltage of the system may vary as necessary to determine that the precise current is transmitted. Thus, any unplanned resistance variations which may be found in collectors 60 do not interfere with the transmission of the signal from electronic block 66 to control system 64. Control system 64 monitors the value of the current in circuit 68, ignoring voltage variations, to provide an absolute, essentially error free readout that is a function of the variable resistance of RTD 62. Accordingly, a precise, quantitative temperature is sensed in accordance with this invention.

Control system 64 may comprise a Fanuc 90-30 PLC controller.

Accordingly, this invention may exhibit unparalleled improvements in accuracy of both data readout and precise creation of desired conditions of temperature and humidity in weathering testing systems, with automated control, but without undesirable fluctuations in the conditions due to feedback problems. Thus, weathering conditions can be precisely duplicated from experimental run to experimental run, facilitating the comparison of results taken in different runs and at different times.

The above has been offered for illustrative purposes only, and is not intended to limit the scope of the invention of this application, which is as defined in the claims below.

That which is claimed is:

1. The method of controlling temperature in a testing chamber having a heater and a variable openable and closable cooling air inlet vent, said method comprising the steps of:

providing a temperature sensor in said chamber to open and close said vent responsive to the temperature sensed by said sensor;

fixing said vent in a first vent position in response to the temperature sensed by said sensor;

controlling said temperature by said heater while said vent is fixed in said first vent position;

said controlling step comprising:
(a) defining a unit of time;
(b) periodically determining the temperature of the air in said chamber;
(c) comparing the difference of the temperature of the air in said chamber with a desired temperature;

(d) activating said heater for a portion of said unit of time, which portion is dependent on the compared temperature difference, while not activating said heater for the remainder of said unit of time; and (e) repeating said process in subsequent units of time.

2. The method of claim 1 in which each unit of time is no more than 30 seconds.

3. The method of claim 2 in which each unit of time is no more than 10 seconds.

4. The method of claim 1 in which each of said units of time are of substantially the same length.

* * * * *